United States Patent [19]

Kung et al.

[11] Patent Number: 4,845,026
[45] Date of Patent: Jul. 4, 1989

[54] ASSAY SYSTEMS FOR DETECTING CELL-FREE T CELL ANTIGEN RECEPTOR RELATED MOLECULES AND THE CLINICAL UTILITIES OF THE ASSAYS

[75] Inventors: Patrick C. Kung, Lexington; Michael C. Brown, Wayland; Stephen H. Ip, Framingham, all of Mass.

[73] Assignee: T Cell Sciences, Inc., Cambridge, Mass.

[21] Appl. No.: 804,289

[22] Filed: Dec. 3, 1985

[51] Int. Cl.$^4$ .............................................. G01N 33/53
[52] U.S. Cl. ............................................ 435/5; 435/7; 436/501; 436/503; 436/504; 436/506; 436/518; 436/548; 436/511; 436/512; 436/813; 436/827
[58] Field of Search ................ 435/7, 5; 436/501, 503, 436/504, 506, 518, 548, 811, 813, 827, 812

[56] References Cited

U.S. PATENT DOCUMENTS 4,526,871 7/1985 Avrameas .......................... 436/827
4,707,443 11/1987 Nelson ................................ 436/531

FOREIGN PATENT DOCUMENTS 8402848 8/1984 PCT Int'l Appl. ..................... 435/7

OTHER PUBLICATIONS

Rubin, J of Immunology 135(5), 1985, pp. 3172–3177.
Fujimoto, J Exp. Med. 159, pp. 752–766 (1983).
Tutt, J of Immunology 137, pp. 2298–3001 (1986).
Allison et al., J. Immunol. 129, 2293–2300 (1982).
Kappler et al., Cell 35, 295–302 (1983).
Acuto et al., J. Exp. Med. 158, 1368–1373 (1983).
Haskins et al., J. Exp. Med. 157, 1149–1169 (1983).
Acuto et al., Cell 34, 717–726 (1983).
McIntyre and Allison, Cell 34, 739–746 (1983).
Reinherz et al., Immunological Reviews 81, 95–129 (1984).
Samelson and Schwartz, Immunological Reviews 81, 131–144 (1984).
Hedrick et al., Nature 308, 153–158 (1984).
Yanagi et al., Nature 308, 145–149 (1984).
Saito et al., Nature 309, 757–762 (1984a).
Saito et al., Nature 312, 36–40 (1984b).
Sim et al., Nature 312, 771–775 (1984).
Chien et al., Nature 312, 31–35 (1984).
Siu et al., Cell 37, 393–401 (1984).
Patten et al., Nature 312, 40–46 (1984).
Kranz et al., Nature 313, 752–755 (1985).
Lefranc and Rabbitts, Nature 316, 464–466 (1985).
Murre et al., Nature 316, 549–552 (1985).
Yanagi et al., Proc. Natl. Acad. Sci. U.S.A. 82, 3430–3434 (1985).
Becker et al., Nature 317, 430–434 (1985).
Hayday et al., Cell 40, 259–269 (1985).
Tonegawa, Scientific American, pp. 122–131 (Oct. 1985).
Caccia et al., Cell 37, 1091–1099 (1984).
Kranz et al., Science 227, 941–944 (1985).
Boylston et al., Eur. J. Immunol. 14, 273–275 (1984).
Brenner et al., J. Exp. Med. 160, 541–551 (1984).
Acuto et al., J. Exp. Med. 161, 1326–1343 (1985).
Bigler et al., J. Exp. Med. 161, 1450–1463 (1985).
Spits et al., J. Immunol. 135, 1922–1928 (1985).
Rao et al., Cell 36, 879–888 (1984).
Bixler and Atassi, Biotechnology 3, 47–54 (1985).
Watts et al., Proc. Natl. Acad. Sci. U.S.A. 82, 5480–5484 (1985).
Bialy, Biotechnology 3, 858 (1985).
Reinherz et al., Cell 30, 735–743 (1982).
Borst et al., J. Biol. Chem. 258, 5135–5141 (1983).
Reinherz et al., Proc. Natl. Acad. Sci. USA 80, 4104–4108 (1983).
Meuer et al., J. Exp. Med. 157, 705–719 (1983).
Oettgen et al., J. Biol. Chem. 259, 12039–12048 (1984).
Weiss and Stobo, J. Exp. Med. 160, 1284–1299 (1984).
Allison and Lanier, Nature 314, 107–109 (1985).
Brenner et al., Cell 40, 183–190 (1985).
Van den Elsen et al., Proc. Natl. Acad. Sci. U.S.A. 82, 2920–2924 (1985).
Ohashi et al., Nature 316, 606–609 (1985).
Krawinkel et al., Cold Spring Harb. Symp. Quant. Biol. 4, 285–294 (1976).
Binz and Wigzell, Cold Spring Harb. Symp. Quant. Biol. 4, 275–284 (1976).
Binz and Wigzell, J. Exp. Med. 154, 1261–1278 (1981).
Ritz et al., Science 228, 1540–1543 (1985).
Robertson, Nature 317, 768–771 (1985).
Taniguchi and Takei, Nature 283, 227–228 (1980).
Rosenstein et al., Proc. Natl. Acad. Sci. U.S.A. 78, 5821–5825 (1981).
Fresno et al., J. Exp. Med. 155, 981–983 (1982).
Krupen et al., Proc. Natl. Acad. Sci. U.S.A. 79, 1254–1258 (1982).
Reinherz et al., U.S. Pat. No. 4,550,086, filed Feb. 16, 1983.
Urdal et al., U.S. Pat. No. 4,578,335, filed May 21, 1984.

Primary Examiner—Robert J. Warden
Assistant Examiner—Robert Benson
Attorney, Agent, or Firm—Pennie & Edmonds

[57] ABSTRACT

Methods are provided for detecting and determining the amount in a sample of an antigenic determinant from an antigen receptor derived and released from a T cell or NK cell. Methods are also provided for detecting and determining the amount in a sample of an antigenic determinant from a complex of at least a portion of an antigen receptor derived from and released from a T cell or NK cell and a protein complex. These methods form the bases for methods of diagnosing and monitoring in a subject a disease characterized by the presence or an amount different from a normal subject of one of these antigenic determinants in a body fluid. A soluble antigen receptor or complex thereof derived from a T cell or a NK cell but free of such T cell or NK cell is also provided.

29 Claims, No Drawings

ASSAY SYSTEMS FOR DETECTING CELL-FREE T CELL ANTIGEN RECEPTOR RELATED MOLECULES AND THE CLINICAL UTILITIES OF THE ASSAYS

BACKGROUND OF THE INVENTION

Within this application several publications are referenced by Arabic numerals within parentheses. Full citations for theses references may be found at the end of the specification immediately preceding the claims. The disclosures of these publications in their entirety are hereby incorporated by reference into this application in order to more fully describe the state of the art to which this invention pertains.

The primary cells of the immune system are the small white blood cells, called lymphocytes, derived from stem cells in the bone marrow. The differentiation of one class of lymphocytes is completed in the thymus gland. Accordingly, these lymphocytes are called T cells.

T cells circulate through the blood and lymphatic vessels of the body and are able to detect and react against foreign invaders, allergens, tumors and auto antigens. Despite their uniform morphology observed under the microscope, T cells consist of a heterogeneous population of three major subsets: the cytotoxic cells that destroy virus-infected cells; and two subsets, designated helper and suppressor cells, which regulate the antibody producing B cells.

A T cell clone is a T cell from which a population of identical T cells is derived by clonal expansion.

The molecular nature of the T cell antigen receptor was reported in the early 1980's by several research groups (1, 2, 3). As shown in these reports the T cell antigen receptor is a heterodimeric glycoprotein composed of two glycosylated polypeptides, one of which is designated the alpha chain and the other of which is designated the beta chain. A T cell antigen receptor is normally present on the surface of each T cell. Each T cell recognizes a single antigenic determinant in association with a protein of a major histocompatibility complex (MHC protein). All T cells derived from a T cell clone contain identical T cell antigen receptors and recognize the same antigenic determinant in association with the same MHC protein.

The alpha and beta chains of the T cell antigen receptor of a T cell clone are each composed of a unique combination of domains designated variable (V), diversity (D), joining (J) and constant (C) (4, 5). In each T cell clone the combination of V, D and J domains of both the alpha and the beta chains participates in antigen recognition in a manner which is uniquely characteristic of that T cell clone and defines a unique binding site, also known as the idiotype of the T cell clone. In contrast the C domain does not participate in antigen binding.

In addition to the alpha and beta chains, a third distinct gene, designated T cell receptor gamma gene, has been isolated. The sequence and organization of the gamma gene are similar to immunoglobulin genes and genes for the alpha and beta chain of the T cell antigen receptor (6). The gamma gene is expressed only in T cells. Tonegawa and coworkers suggest that T cell antigen receptors of some T cells are made up of a gamma chain and a beta chain (7).

The alpha and beta chains of the T cell antigen receptor of a T cell clone also define a plurality of antigenic determinants which can be recognized by antibodies directed to the antigen receptor. An antibody which reacts solely with the T cell clone or inhibits antigen binding only to the antigen receptor of the T cell clone against which it is raised is defined to be anti-idiotypic (2, 8, 9). If an antigenic determinant defined by the alpha or beta chains, or both, is present on the surface of, or associated with, a relatively limited number of T cell clones, the determinant is designated a minor framework determinant of the T cell antigen receptor(9, 10). If an antigenic determinant defined by the alpha or beta chain, or both, is present on the surface of, or associated with, a relatively large number or all T cell clones, the determinant is designated a major framework determinant of the T cell antigen receptor (11).

Although the demarcation between being present on a relatively limited number of T cell clones and being present on a relatively large number or all T cell clones is not always precise, those skilled in the art to which this invention pertains fully understand and appreciate this demarcation and can readily classify most given antigenic determinants as being either a minor or a major framework determinant. For purposes of this application any antigenic determinant as to which those skilled in the art would not concur is defined to be a minor framework determinant. In general antibodies to major framework determinants will recognize at least 20% of the peripheral T cells of a normal subject and antibodies to minor framework determinants will recognize less than 20% of the peripheral T cells of a normal subject. By contrast, recognition of peripheral T cells of normal subjects by anti-idiotypic antibodies will not be detectable.

Natural Killer (NK) cells, although lacking most of the surface differentiation antigens associated with the three major subsets of T cells, have been confirmed as members of the T cell lineage and are considered by many a subset of T cells. NK cells are characterized by their ability to mediate direct cytotoxicity against specific target cells, e.g. cancer cells, without apparent prior immunization (12 13). It has been observed that some NK cells have on their surfaces a heterodimeric receptor capable of antigen recognition without specific MHC protein associations. For purposes of this application, unless otherwise stated, all references to antigen receptors shall include heterodimeric antigen receptors derived from the surface of T cells and NK cells.

It has been suggested that the T cell antigen receptor is noncovalently associated with the T3 protein complex on the membrane (14). The T3 protein complex is composed of three distinct membrane associated polypeptide chains known as T3-gamma, T3-delta and T3-epsilon (15). This T3 protein-antigen receptor association can be demonstrated by immunoprecipitation studies with antibodies against the T3 protein complex and by comodulation or mutant studies in which the antigen receptor and the T3 protein complex may co-disappear or co-appear on the membrane (16).

Heretofore the measurement of T cell antigen receptors has been limited to the detection of T cell-associated antigen receptors by a variety of immunological techniques involving monoclonal antibodies against the antigen receptor. Such measurements have been routinely accomplished by binding fluorescence conjugated monoclonal antibodies to T cells followed by cellular analysis with a fluorescent-activated cell sorter or similar flow cytometer (9). Such cell analysis provides information about the percent of T cells expressing the receptor in a given sample, however the accuracy and reliability of such routine analysis is limited to 1–2% or more of positive cells in a sample using existing flow cytometers. Furthermore the cell analysis is tedious and often requires fresh, live cells and a skilled, dedicated operator.

The molecular mechanism of T cell antigen receptor-antigen interaction is a subject of intensive investigation (13). It has been shown (17) that T cell clones are capable of binding membrane bound antigens associated with MHC proteins. Rao, et al. (28) reported however that some antigens can bind to the antigen reactive T cell clones in the absence of a MHC protein. In a recent report (18) on ligand binding to the T cell antigen receptor, recombinant DNA techniques were used to prepare a hybrid molecule with T cell antigen receptor regions contained within immunoglobulin frameworks. However, no immunological reactivities against the hybrid molecules were described therein.

Between 1975–1981, a series of papers were published on the characterization of "T cell antigen receptors" in mouse and rat systems (19,20,21). These "T cell antigen receptors" are not the "T cell antigen receptor" described herein (see references 1,2,3,6,26). References 19,20, and 21 describe a protein, designated "T cell antigen receptor", with a molecular weight of approximately 150,000–180,000 daltons. This "antigen receptor" is further characterized as a dimer with a protein subunit having a molecular weight of about 70,000 daltons. The chromosomal location of this "antigen receptor's" variable region in mice is on chromosome 12 (21). The T cell antigen receptor described within this application has a molecular weight of about 90,000 daltons (1,2,3). Furthermore, the subunit structures of this antigen receptor consist of three heterodimeric glycosylated polypeptides, designated the alpha, beta, and gamma chains, having molecular weights in mans of approximately 45,000 daltons (2), 40,000 daltons (2), and 30,000 daltons, respectively. The chromosomal locations of the variable regions in mice are: alpha, chromosome 14 (26); beta, chromosome 6 (27); and gamma, chromosome 13 (26).

In 1982, it was reported that the external shedding of the T3 protein by human T cell clones could be artificially induced by adding an anti-T3 protein antibody to these T cells in culture. However, no observation of the spontaneous shedding or release of T3 protein, in vivo or in vitro, was noted (22).

Fujimoto et al. (23) developed an enzyme-linked immunoabsorbent assay (ELISA) for the detection of human T cell surface antigens in soluble form. When sera and culture supernatants from various cell lines were tested, Leu-2 antigen, but not Leu-1 or Leu-3, was found to be present. Applicants are also aware of the pending U.S. patent application, U.S. Ser. No. 724,897, filed Apr. 19, 1985 in the name of David Nelson et al., assigned to the U.S. Government and entitled "Soluble Interleukin-2 Receptor As A Disease Indicator And A Method of Assaying The Same." This patent application, based on the findings of Rubin et al. (24), concerns soluble or released Interleukin-2 Receptor, which is believed to interact with the T cell growth factor Interleukin-2. However, neither the Fujimoto publication, the Nelson patent application, or the Rubin publication discloses or teaches the existence of a released T cell antigen receptor and methods for detecting and measuring it in a biological fluid.

The present invention concerns the discovery of antigen receptors and molecules derived therefrom which are released or present in soluble form in a biological fluid, i.e. they are not bound to a T cell or NK cell. Specific T cell antigen receptors are spontaneously released from the T cells at different metabolic rates under disease conditions than under normal conditions, and become accumulated in body fluids. Rapid, sensitive and inexpensive methods for determining the amount of released antigen receptor or complex thereof in a body fluid are provided. These methods are useful for diagnosing and monitoring diseases in a subject.

Furthermore, a plurality of T cell clones in an individual can simultaneously respond to more than one pathogen (30). Thus it is contemplated that the serum from the individual contains a mixture of distinct types of released T cell antigen receptors. The quantitative measurement of each type of the released receptor allows the diagnosis and monitoring of a patient with multiple infections or a disease involving a plurality of pathogens.

It is well known that both T cells and B cells recognize antigens with specificity (7, 13). Although it is established that T cells, unlike B cells, recognize antigens in association with MHC proteins, it is not clear whether antigenic sites on an antigen which are recognizable by T cells or B cells are related. In a recent report, G.S. Bixler and M.Z. Atassi (25) concluded that the regions of a protein molecule recognized by B cells (antibody binding) may also be recognized by T cells. T cells, however, may recognize additional areas of the molecule to which no detectable antibody responses have thus far been observed. These data suggest that the unique aspect of T cell recognition is useful for detecting disease antigens in diagnostic and therapeutic applications (25). The existence of soluble T cell antigen receptors disclosed herein provides a novel source of reagents for these applications.

SUMMARY OF THE INVENTION

The present invention provides a method for detecting in a sample an antigenic determinant from an antigen receptor derived and released from a T cell or NK cell which comprises contacting the sample with a suitable reagent so as to form a reaction complex between the reagent and the antigenic determinant, detecting the presence of the reaction complex so formed and thereby detecting the antigenic determinant.

This method may be used for diagnosing in a subject a disease characterized by the presence in a body fluid of the subject of an antigenic determinant from an antigen receptor derived and released from a T cell or NK cell and indicative of the disease.

Additionally, this method may be used for monitoring in a subject a diseased condition characterized by the presence in a body fluid of the subject of an antigenic determinant from an antigen receptor derived and released from a T cell or NK cell and indicative of the disease. Such monitoring may be performed by identifying and correlating the presence or absence of the antigenic determinant in a body fluid over a period of time with the diseased condition.

A method is also provided for detecting in a sample an antigenic determinant from a complex of at least a portion of an antigen receptor derived and released from a T cell or NK cell and a protein complex. This method comprise contacting the sample with a suitable reagent so as to form a reaction complex between the reagent and the antigenic determinant, determining the presence of the reaction complex so formed and thereby detecting the antigenic determinant. This method may also be used for diagnosing in a subject a disease characterized by the presence in a body fluid of the subject of an antigenic determinant from the antigen receptor of a T cell or NK cell and a protein complex and indicative of the disease.

Methods are provided for quantitatively determining in a sample the amount of an antigenic determinant from an antigen receptor derived and released from a T cell or NK cell and an antigenic determinant from a complex of at least a portion of an antigen receptor derived and released from a T cell or N cell and a protein complex. These methods comprises contacting the sample with a known amount of a suitable reagent so as to form a reaction complex between the reagent and the antigenic determinant, determining the amount of the reaction complex so formed and determining therefrom the amount of the antigenic determinant in the sample.

The present invention also concerns methods of diagnosing in a subject a disease. One method involves diagnosing a disease characterized by the presence in a body fluid of the subject of an amount of an antigenic determinant from an antigen receptor derived and released from a T cell or NK cell, which amount is different from the amount of the antigenic determinant present in the body fluid of a normal subject and is indicative of the disease. Another method involves a disease characterized by the presence in the body fluid of the subject of an amount of an antigenic determinant from at least a portion of an antigen receptor derived and released from a T cell or NK cell and a protein complex, which amount is different from the amount of the antigenic determinant present in the body fluid of a normal subject and is indicative of the disease. These methods comprise contacting a sample of the body fluid with a known amount of a suitable reagent so as to form a reaction complex between the reagent and the antigenic determinant, determining the amount of the reaction complex so formed, determining therefrom the amount of antigenic determinant in the sample comparing the amount of the antigenic determinant so determined with the amount present in a sample from a normal subject, and thereby diagnosing the disease.

A method of monitoring in a subject a diseased condition is also provided. This method involves monitoring a diseased condition characterized by the presence in a body fluid of the subject of an amount of an antigenic determinant from an antigen receptor derived and released from a T cell or NK cell and indicative of the disease condition.

The present invention further provides a soluble antigen receptor, or complex thereof, derived from a T cell or a NK cell but free of such T cell or NK cell. It is contemplated that the released antigen receptor or complex thereof comprises immunomodulating activity.

The invention also provides a method for diagnosing in a subject a disease characterized by the presence in a body fluid of the subject of an amount of an antigenic determinant from an antigen receptor derived and released from a T cell or NK cell, which amount is different from the amount of the antigenic determinant present in a body fluid of a normal subject and is indicative of the disease. This method comprises contacting a sample of the subject's body fluid with a known amount of an antigen capable of binding to the antigenic determinant under suitable conditions so as to form a reaction complex between the antigen and the antigenic determinant, determining the amount of reaction complex so formed, determining therefrom the amount of antigenic determinant in the sample, comparing the amount of the antigenic determinant so determined with the amount present in a sample from a normal subject, and thereby diagnosing the disease.

DETAILED DESCRIPTION OF THE INVENTION

The present invention provides a method for detecting in a sample an antigenic determinant from an antigen receptor derived and released from a T cell or NK cell. Such antigen receptors may be released from the T cell or NK cell membrane by solubilizing agents, e.g. a nonionic detergent, or more importantly they may be spontaneously released from the cell into its surrounding fluid. The method for detecting the antigenic determinant comprises contacting a sample containing the antigenic determinant with a suitable reagent so as to form a reaction complex between the reagent and the antigenic determinant, detecting the presence of the reaction complex so formed and thereby detecting the antigenic determinant.

This method may be performed on a sample which is a biological fluids. Examples of such biological fluids include blood, plasma, serum, urine, spinal fluid, synovial fluid, amnionic fluid and cranial fluid.

The sample may comprise the entire antigen receptor on which the antigenic determinant is present or a fragment of the antigen receptor, in which case the antigenic determinant is present on said fragment. Both the entire antigen receptor and the fragment of the antigen receptor may be functional, i.e. a T cell antigen receptor capable of binding to an antigen associated with an MHC protein or an NK cell antigen receptor capable of binding to an antigen.

The antigenic determinant may be from the alpha chain, the beta chain, or the gamma chain of the T cell antigen receptor.

The reagent used to form a complex with the antigenic determinant may be labelled with a marker. Such markers include a fluorescent dye, a radioactive isotope and an enzyme which catalyses a reaction producing a detectable product. These markers may be detected by using a variety of techniques and instruments known to those skilled in the art, i.e. fluorimeters, liquid scintillation counters and spectrophotometers.

The reagent which forms a complex with the antigenic determinant may be an antibody, a monoclonal antibody or a lectin. Furthermore, the reagent may be an antigen.

The antigen determinant to be detected may be on the antigen receptor of more than 20% of all T cells or NK cells. Such an antigenic determinant may form a complex with a reagent which is an anti-major framework antibody. Additionally, the antigenic determinant may be on the antigen receptor of less than 20% of all T cells or NK cells. Such an antigenic determinant may form a complex with a reagent which is an anti-minor framework antibody. Moreover, the antigenic determinant may be on the antigen receptor of one T cell clone or NK cell clone, and may form a complex with a reagent which is an anti-idiotypic antibody.

The antigenic determinant may be on a complex which comprises a protein complex. In a preferred embodiment of the invention the protein complex is the T3 protein complex.

The present invention also provides a method for detecting in a sample an antigenic determinant from a complex of at least a portion of an antigen receptor derived and released from a T cell or NK cell and a protein complex. This method comprises contacting the sample with a suitable reagent so as to form a reaction complex between the reagent and the antigenic determinant, detecting the presence of the reaction complex so formed and thereby detecting the antigenic determinant.

The antigenic determinant to be detected by this method may be on the protein complex. In a preferred embodiment of the invention, the protein complex is the T3 protein complex and the reagent used to form a reaction complex with the antigenic determinant is an anti-T3 antibody.

The present invention also provides a method for diagnosing in a subject a disease characterized by the presence in a body fluid of the subject of an antigenic determinant from the antigen receptor of a T cell or NK cell and indicative of the disease. By detecting the presence of the antigenic determinant in a sample of the subject's body fluid according to a method of the present invention, the disease may be diagnosed. The subject may be an animal or a human.

The disease which is diagnosed may be a form of cancer, an autoimmune disease, an allergy or an infectious disease. Furthermore, the infectious disease may be caused by a virus, fungus, parasite or bacterium.

The present invention further provides a method for diagnosing in a subject a disease characterized by the presence in a body fluid of the subject of an antigenic determinant from a complex of at least a portion of the antigen receptor derived and released from a T cell or NK cell and a protein complex, said complex being indicative of the disease. By detecting the presence of such a complex in a sample of the subject's body fluid according to a method of the present invention, the disease may be diagnosed.

A method is also provided for monitoring in a subject a diseased condition characterized by the presence in a body fluid of the subject of an antigenic determinant from an antigen receptor derived and released from a T cell or NK cell and indicative of the diseased condition. This method comprises identifying the presence or absence of the antigenic determinant in a series of body fluid samples, taken over a period of time, according to a method of the present invention. The presence or absence of the antigenic determinant in the body fluid samples is correlated with the diseased condition of the subject.

A method for quantitatively determining in a sample the amount of an antigenic determinant from an antigen receptor derived and released from a T cell or NK cell is also provided. This method comprises contacting the sample with a known amount of a suitable reagent so as to form a reaction complex between the reagent and the antigenic determinant, determining the amount of the reaction complex so formed and determining therefrom the amount of the antigenic determinant in the sample.

The present invention further provides a method for quantitatively determining in a sample the amount of an antigenic determinant from a complex of at least a portion of an antigen receptor derived and released from a T cell or NK cell and a protein complex. The amount of the antigenic determinant in the sample is determined by contacting the sample with a known amount of a suitable reagent so as to form a reaction complex between the reagent and the antigenic determinant, determining the amount of reaction complex so formed and determining therefrom the amount of the antigenic determinant in the sample.

Additionally, a method is provided for diagnosing in a subject a disease characterized by the presence in a body fluid of the subject of an amount of an antigenic determinant from an antigen receptor derived and released from a T cell or NK cell, which amount is different from the amount of the antigenic determinant present in the body fluid of a normal subject and is indicative of the disease. This method comprises contacting a sample of the subject's body fluid with a known amount of a suitable reagent so as to form a reaction complex between the reagent and the antigenic determinant, determining the amount of reaction complex so formed, determining therefrom the amount of antigenic determinant in the sample, comparing the amount of the antigenic determinant so determined with the amount present in a sample from a normal subject and thereby diagnosing the disease.

The body fluid in which the antigenic determinant is present may be blood, plasma, serum, urine, spinal fluid, synovial fluid, amnionic fluid, or cranial fluid, and the subject may be an animal or a human.

It is contemplated that a multiplicity of diseases may be concurrently diagnosed by concurrently diagnosing each such disease by a method of this invention.

The body fluid may comprise the entire antigen receptor from which the antigenic determinant is derived, or the antigenic determinant may be present in the body fluid on a fragment of the antigen receptor. Both the entire antigen receptor and the fragment of the antigen receptor may be functional. Additionally, the antigenic determinant may be from the alpha chain, the beta chain, or the gamma chain of a T cell antigen receptor.

The reagent may be an antibody, monoclonal antibody, lectin, or antigen labelled with a marker such as a fluorescent dye, a radioactive isotope or an enzyme which catalyses a reaction producing a detectable product.

The antigenic determinant may be on the antigen receptor of more than 20% of all T cells or NK cells. Such an antigenic determinant may form a complex with a reagent which is an anti-major framework antibody. Additionally, the antigenic determinant may be on the antigen receptor of less than 20% of all T cells or NK cells. Such an antigenic determinant may form a complex with a reagent which is an anti-minor framework antibody. Furthermore, the antigenic determinant may be on the antigen receptor of one T cell clone or NK cell clone. This antigenic may form a complex with a reagent which is an anti-idiotypic antibody.

The antigenic determinant may be on a complex which comprises a protein complex. In a preferred embodiment of the invention the complex is the T3 protein complex.

This quantitative diagnostic method may be performed as a sandwich assay which comprises determining the amount of the antigenic determinant in the body fluid by contacting the sample with a suitable immobilized first reagent so as to form a reaction complex between the reagent and the antigenic determinant, contacting the reaction complex so formed with a known amount of a suitable second reagent labelled with a marker so as to form a second reaction complex among the first reagent, the second reagent and the antigenic determinant, determining the amount of second reaction complex so formed, determining therefrom the amount of the antigenic determinant in the sample and thereby diagnosing the disease. The first reagent may be immobilized onto a solid plastic phase, such as a microtiter plate, although other phases known by those skilled in the art, such as plastic beads or plastic tubes, would work as well.

The first reagent of this sandwhich technique may be an anti-major framework antibody and the second reagent may be an anti-receptor antibody, i.e. an anti-major framework, anti-minor framework, or an anti-idiotypic antibody, or a lectin. Additionally, the first reagent may be an anti-minor framework antibody and the second reagent may be an anti-receptor antibody or a lectin. Furthermore, the first reagent may be an anti-idiotypic antibody and the second reagent may be an anti-receptor antibody or a lectin.

The disease which is diagnosed by this method may be a form of cancer, an autoimmune disease, an allergy or an infectious disease. Furthermore, the infectious disease may be caused by a virus, fungus, parasite or bacterium.

A method is also provided for diagnosing in a subject a disease characterized by the presence in a body fluid of an amount of an antigenic determinant from a complex of at least a portion of an antigen receptor derived and released from a T cell or NK cell and a protein complex, which amount is different from the amount of the antigenic determinant present in the body fluid of a normal subject and is indicative of the disease. This method comprises contacting a sample of the subject's body fluid with a known amount of a suitable reagent so as to form a reaction complex between the reagent and the antigenic determinant, determining the amount of reaction complex so formed, determining therefrom the amount of antigenic determinant in the sample, comparing the amount of antigenic determinant so determined with the amount present in a sample from a normal subject, and thereby diagnosing the disease. The antigenic determinant may be on the protein complex. In a preferred embodiment of the invention, the protein complex is the T3 protein complex.

It is contemplated that this method of diagnosis encompasses the body fluids, subjects, suitable reagents, detectable markers, and diseases discussed previously within this application.

This diagnostic method may also be performed as a sandwich assay which comprises determining the amount of the antigenic determinant in the body fluid by contacting the sample with a suitable immobilized first reagent so as to form a reaction complex between the reagent and the antigen receptor complex, contacting the reaction complex so formed with a known amount of a suitable second reagent labelled with a marker so as to form a second reaction complex among the first reagent, the second reagent and the antigen receptor complex, determining the amount of second reaction complex so formed, determining therefrom the amount of the antigenic determinant in the sample and thereby diagnosing the disease.

The first reagent of this sandwich technique may be an anti-receptor antibody, i.e. an anti-major framework, anti-minor framework, or anti-idiotypic antibody and the second reagent may be anti-receptor antibody, an anti-T3 antibody, or a lectin. Additionally, the first reagent may be an anti-T3 antibody and the second reagent may be anti-receptor antibody, an anti-T3 antibody, or a lectin.

The present invention also provides a method of monitoring in a subject a diseased condition characterized by the presence in a body fluid of an amount of an antigenic determinant from an antigen receptor derived and released from a T cell or NK cell and indicative of the diseased condition. Such a method of monitoring a disease comprises determining, by a method of this invention, the amount of the antigenic determinant present in a series of body fluid samples taken over a period of time, identifying changes in the amount of the antigenic determinant in the body fluid over time and correlating said changes with the diseased condition of the subject.

The present invention further provides a soluble antigen receptor, or complex thereof, derived from a T cell or a NK cell but which is free of such T cell or NK cell. This antigen receptor may be bound to a protein complex, e.g. the T3 complex, or a therapeutic chemical. The antigen receptor may also be labelled with a marker such as a fluorescent dye, a radioactive isotope or an enzyme which catalyses a reaction producing a detectable product.

In certain embodiments of the invention, the antigen receptor is functional, i.e. capable of antigen binding and having immunomodulating activity, although this may not always be true in all cases. In other embodiments, the antigen receptor may be purified by methods which are well known in the art, e.g affinity chromatography or with recombinant DNA prepared receptor proteins.

A method is also provided for detecting an antigen in a sample by contacting the sample with a suitable antigen receptor of the present invention so as to form a reaction complex between the antigen receptor and the antigen, detecting the reaction complex so formed and thereby detecting the presence of the antigen. This method may be used to diagnose a disease in a subject by detecting in a body fluid of the subject an antigen associated with the cause of the disease.

The present invention further provides a method for diagnosing in a subject a disease characterized by the presence in a body fluid of the subject of an amount of an antigenic determinant from an antigen receptor derived and released from a T cell or NK cell, which amount is different from the amount of the antigenic determinant present in the body fluid of a normal subject and is indicative of the disease. This method comprises contacting a sample of the subject's body fluid with a known amount of an antigen capable of binding to the antigenic determinant under suitable conditions so as to form a reaction complex between the antigen and the antigenic determinant, determining the amount of reaction complex so formed, determining therefrom the amount of antigenic determinant in the sample, comparing the amount of the antigenic determinant so determined with the amount present in a sample from a normal subject, and thereby diagnosing the disease.

The antigen used to form the reaction complex with the antigenic determinant may be associated with a major histocompatibility complex protein. Additionally either the antigen or the major histocompatibility complex protein may be labelled with a marker.

EXPERIMENTAL RESULTS

Detection of Spontaneously Released T Cell Antigen Receptor and T Cell Antigen Receptor Complex in T Cell Culture Supernatant T cell lines and B cell lines, obtainable from the American Type Culture Collection (ATCC) or many university laboratories, were grown and maintained in RPMI 1640 (a culture fluid purchased from Gibco Laboratories, Grand Island, N.Y.) with 10% fetal calf serum at 37° C. and 5% CO. Culture supernatants were harvested from log growth phase cultures of these cell lines at a cell density of 1 million cells per millimeter. In all cases viabilities were greater than 99%. Supernatants were freed of membrane fragments by centrifugation at 50,000×G for one hour. In some instances an additional step consisting of filtration through a 0.22 μm filter (Arco LC13, Gelman Sciences, Ann Arbor, Michigan) was used.

As previously discussed, there are at least three distinct types of antibodies against T cell antigen receptors, namely, the anti-major framework, anti-minor framework, and anti-idiotypic antibodies. The cellular reactivities of a representative antibody of each type are shown in Table I.

TABLE I
Reactivity of Cell Lines with Distinct types of Anti-T Cell Antigen Receptor Monoclonal Antibodies*

| Cell Line | Antibody Reactivity* | | |
|---|---|---|---|
| | Anti-Major Framework | Anti Minor Framework (% positive) | Anti-Idiotype (% positive) |
| HPB-ALL T cell (leukemia) | + | 80%–100% | 80%–100% |
| Jurkat T cell (lymphoma) | + | 0 | 0 |
| CEM T cell (leukemia) | + | 0 | 0 |
| Daudi B cell (lymphoma) | − | 0 | 0 |
| Peripheral T Cells Of A Normal Subject | + | 1%–5% | 0 |

*The reactivities were studied by cellular immunofluorescence or by immunoprecipitation. Examples of anti-bodies used: Anti-idiotype, references 2, 8 and 9; Anti-minor framework, reference 10; Anti-major framework, references 10 and 11.

The anti-major framework antibody reacted with all T cells, but not with the B cells. The anti-minor framework antibody reacted with one leukemia (HPB-ALL) T cell line and some peripheral T cells, but not with another lymphoma (Jurkat) T cell line, a leukemic (CEM) T cell line, or a lymphoma (Daudi) B cell line. The anti-idiotypic antibody reacted only with the specific T cell line against which it was raised, i.e. the HPBALL T cell line.

The following experiments were designed and performed to test whether soluble T cell antigen receptors are spontaneously released by cultured T cells. Microtiter plates (Immulon I, purchased from Dynatech, Alexandria, Virginia) were coated (immobilized) overnight at 4° C. with an anti-receptor antibody at 2.5 μg/ml in phosphate buffered saline (PBS). The next day the plates were treated with 1% bovine serum albumin (BSA) to block any remaining sites on the plate to which protein might be non-specifically absorbed. Plates were then washed with 10 mM Tris pH 8.0 in 0.05% polyoxyethylenesorbitan monolaurate (Tween 20, purchased from Sigma Chemical Company, St. Louis, Mo.).

One hudnred microliters of culture supernate were diluted with a suitable buffer (e.g., 0.01 M Tris, 0.15 M NaCl, 1 mM MgCl$_2$, 1 mM phenylmethylsulfonyl-fluoride (PMSF), 10 mM iodoacetamide, 1 μg/ml pepstatin and 10 μg/ml N-tosyl-L-phenylalanine chloromethyl ketone (TCPK), pH 8.0 containing Nonidet P-40 (NP40, an ionic detergent comprising an octyl phenol ethylene oxide condensate containing an average of 9 moles ethylene oxide per molecule, purchased from Sigma Chemical Company) at 1.0%), added to the coated microtiter wells and incubated at 37° C. for two hours. Unbound sample was washed away and 100 μl of a properly titered amount of a biotinylated second detection antibody directed against the T cell antigen receptor was added. Following a second incubation at 37° C. for two hours, unbound biotinylated antibody was washed away and 100 μl of a properly titered amount of a conjugate of streptavidinhorseradish (purchased from Zymed Laboratories, San Francisco, Calif.) peroxidase was added and incubated for 30 minutes at 37° C. Unbound conjugate was washed away and freshly made substrate (0.2% of dihydrochloride orthophenylenediamine in buffered peroxide consisting of 0.015% hydrogen peroxide, 65mM disodium phosphate, 17mM citric acid pH 5.5) was added. After incubation at 37° C. for 20 minutes, the reaction was stopped by the addition of 15 μl of 2N sulfuric acid and the color developed in the microtiter well was read at 490 nm (OD 490) on a ELISA reader (MR 600, purchased from Dynatech).

Appropriate controls consisted of: (1) microtiter wells to which no first coating antibody had been added, to account for nonspecific binding of the sample to plate; (2) samples from a B cell line or sera from a normal subject to account for nonspecific binding of the first coating antibody to the sample; and (3) nonrelevant antibodies with the same immunoglobulin isotype of the coated and detection antibodies to control for nonspecific binding of either sample to the coated antibody or the detection antibody to the plate or sample.

The results of these assays are shown in Table II below.

TABLE II
Detection of Spontaneously Released T Cell Antigen Receptor

| Source of Culture Supernatant | Sample Treatment | Anti-Major Framework Detection OD$_{490}$ | Anti-Idiotype Detection OD$_{490}$ |
|---|---|---|---|
| HPB-ALL T cell line (leukemia) | None | 0.010 | 0.005 |
| | 0.1% NP40 | 0.123 | 0.171 |
| CEM T cell line (leukemia) | None | 0.006 | 0.005 |
| | 0.1% NP40 | 0.009 | 0.020 |
| Jurkat T cell line (lymphoma) | None | 0.010 | 0.000 |
| | 0.1% NP40 | 0.014 | 0.019 |
| Daudi B cell line (lymphoma) | None | 0.007 | 0.000 |
| | 0.1% NP40 | 0.006 | 0.000 |

Culture supernatants were harvested from log phase cultures and freed of membrane fragments by centrifugation (50,000 × G for 1 Hour) and filtration (0.22 μm). 100 μl of each culture supernatant was analyzed with and without detergent using an anti-minor framework region antibody as the immobilized reagent and an anti-major framework or anti-idiotype antibody as the detection reagent.

From Table II, several conclusions can be drawn. First, the existence of the spontaneously released T cell antigen receptor in the HPB-ALL T cell culture supernatant can be demonstrated only under suitable conditions, e.g. when the cell-free samples were treated with 0.1% NP40, a nonionic detergent. Second, the anti-minor framework antibody coated on the plate is only reactive, as with cellular immunofluorescence (see Table I supra), with the HPB-ALL T cell line, and not with the CEM and Jurkat T cell lines or the Daudi B cell lines. The data in Table II confirm this specificity because only released receptors from the HPB-ALL leukemia T cells were quantifiable using a detection antibody such as an anti-major framework antibody or an anti-idiotypic antibody. This data, indicates the released antigen receptor is related to the membrane antigen receptor. Third, it is contemplated that the released T cell antigen receptor can also be detected by using two distinct anti-major framework or anti-minor framework antibodies in the sandwich immunoassay, provided that they do not compete for the same binding site. It is also contemplated that some of the released T cell antigen receptor is detectable by using the same anti-receptor antibody for the coated as well as the detection antibody under some conditions, e.g. the existence of a multiplicity of antigenic determinants in the receptor preparation. It is additionally contemplated that, depending on the nature of the antigenic determinant on the receptor, the type and concentration of a detergent may be important in these assays.

To determine whether at least some of the released T cell antigen receptor is associated with the T3 protein complex, as it has been shown to exist on the T cell membrane (14, 16)), supernatants were assayed using an anti-T3 antibody, such as OKT3 obtainable from Ortho Diagnostic Systems, Raritan, N.J. or Leu4 obtainable from Becton Dickinson Monoclonal Center, Mountainview, California, as the coated antibody, i.e. immobilized on the microtiter plate as described supra. Supernatants were assayed untreated, treated with the detergent NP40 at a final concentration of 0.2%, or treated with the detergent digitonin (purchased from Aldrich Chemical Company, Milwaukee, Wis.) at a final concentrate of 0.2%. The results are shown in Table III below.

TABLE III

Detection of Spontaneously Released T Cell Antigen Receptor Complex

| Source of Culture Supernatant | Sample Treatment | Anti-Major* Framework Detection OD$_{490}$ | Anti-Idiotype* Detection OD$_{490}$ |
|---|---|---|---|
| HPB-ALL T cell line (leukemia) | None | 0.024 | 0.129 |
|  | 0.2% NP40 | 0.014 | 0.026 |
|  | 0.2% Digitonin | 0.174 | 0.254 |
| Jurkat T cell line (lymphoma) | None | 0.001 | 0.014 |
|  | 0.2% NP40 | 0.003 | 0.017 |
|  | 0.2% Digitonin | 0.128 | 0.036 |
| Daudi B cell line (lymphoma) | None | 0.011 | 0.016 |
|  | 0.2% NP40 | 0.000 | 0.014 |
|  | 0.2% Digitonin | 0.010 | 0.022 |

*Coated with an anti-T3 antibody.

Several significant observations are noted from this data. First, the detection of the receptor complex in the culture supernatant was influenced by the presence of detergents. In the absence of a detergent, significant amounts of the released receptor complex in HPB-ALL supernatant could be measured with the anti-idiotype, whereas in the presence of digitonin the detectable level of the released receptor complex was enhanced and could be measured with ten anti-major framework antibody in both T cell lines tested. However, no complex was detected in the presence of NP40. Second, when an anti-major framework antibody was used as the detection antibody, the supernatants from both the HPB-ALL and the Jurkat T cell lines were shown to contain released receptor. In contrast, when an anti-idiotypic antibody specific to the HPB-ALL T cell line was used as the detection antibody, only the culture supernatant derived from the HPB-ALL T cell line was shown to contain a significant amount of released receptor complex. In neither mode of detection did the control Daudi B lymphoma cell line give a positive result.

A set of experiments was performed to further investigate the effects of detergent treatment on samples, and the effects of different antibodies used as the coated or the detection antibody in the released T cell antigen receptor assay. As shown in Table IV, when an anti-minor framework or an anti-idiotype was used as the coated antibody, HPB-ALL supernatant samples treated with NP40 registered a higher level of released T cell antigen receptor than HPB-ALL supernatant samples treated with digitonin. However, when an anti-T3 antibody was used as the coated antibody, digitonin treated HPB-ALL supernatants registered a higher level of released T cell antigen receptor complex than the NP40 treated samples, although significant amounts of the released receptor complex could also be detected in the absence of any detergent when an anti-idiotype or an anti-minor framework antibody was used as the detection antibody.

TABLE IV

Detection of Spontaneously Released T Cell Antigen Receptor or Receptor Complex In Culture Supernatant of HPB-ALL T Cells

| Coated Antibody | Detection Antibody | | | |
|---|---|---|---|---|
|  | Anti-Idiotype | Anti-Minor Framework | Anti-Major Framework | |
| Anti-Minor Framework | 0.54+ | 0 | 0.145 | NP40* |
|  | 0.066 | 0 | 0.020 | Digitonin* |
|  | (0.005) | (0.007) | (0.014) | no detergent |
| Anti-Idiotype | 0 | 0.329 | 0.221 | NP40 |
|  | 0 | 0.31 | 0.149 | Digitonin |
|  | (0.006) | (Not Done) | (0.011) | no detergent |
| Anti-T3 | 0 | 0 | 0 | NP40 |
|  | 0.251 | 0.167 | 0.216 | Digitonin |
|  | (0.057) | (0.056) | (0) | no detergent |

+OD$_{490}$ value
*Detergent used to treat sample (method previously described herein)

Detection of Released T Cell Antigen Receptor In Cell Lysates

Samples to be analyzed were prepared from solubilized normal mononuclear or leukemic T cell lines and B cell controls in an isotonic buffer (preferably 0.15 M NaCl, 0.01 M Tris pH 7.4, 1 mM MgCl$_2$) containing protease inhibitors (preferably PMSF, TCPK, aprotinin, pepstatin, or iodoacetamide) and a detergent (preferably NP40 or digitonin from 0.1 to 5%, more preferably at 1%, although other chemically related detergents will work as well). Following solubilization, nuclei and other debris were removed by centrifugation (10 minutes, 400×G followed by recentrifugation at 20 minutes, 50,000×G). Lysates were analyzed immediately by the ELISA sandwich assay described in the previous examples or stored at 4° C. or frozen. It is obvious that tissues could be processed in a similar manner in the case of lymphoid tisssue or other tissues infiltrated by lymphocytes (e.g. reference 29).

One hundred microliters of the lysate preparation was analyzed by the procedure described in Table II. As shown below in Table V, the solubilized T cell antigen receptor was detected in the cell lysates of the T cell lines and the peripheral mononuclear cells, but not in the B lymphoma cell (Daudi) lysate. A matrix of coated antibodies and detection antibodies was performed to investigate the effect of antibody in the measurement of released T cell antigen receptors in NP40 treated HPB-ALL lysates. As shown in Table VI, when an anti-minor framework or an anti-major framework antibody was used as both the coated antibody and the detection antibody, a lower but significant level of released T cell antigen receptor could also be measured. It is contemplated that the detection of T cell antigen receptor complex in cell lysate can also be performed by using an anti-T3 antibody as the coated antibody and an anti-receptor antibody as the detection antibody under similar conditions described supra.

TABLE V

Detection of T Cell Antigen Receptor In Cell Lysates

| Cell Type | Cell Equivalents in Assay | | OD 490 |
|---|---|---|---|
| HPB-ALL T Cell line (leukemia) | $2.5 \times 10^5$ | | 1.577 |
| | $1.25 \times 10^5$ | | 0.822 |
| | $6.2 \times 10^4$ | | 0.487 |
| | $3.1 \times 10^4$ | | 0.233 |
| | $1.5 \times 10^4$ | | 0.117 |
| Peripheral Mononuclear Cells+ | $2 \times 10^6$ | $(4 \times 10^4)$ ++ | 0.087 |
| | $5 \times 10^5$ | $(1 \times 10^4)$ ++ | 0.051 |
| | $1.25 \times 10^5$ | $(2.5 \times 10^3)$ ++ | 0.019 |
| Jurkat T Cell line (lymphoma) | $2.5 \times 10^5$ | | 0.020 |
| Daudi B Cell line (lymphoma) | $2.5 \times 10^5$ | | 0.000 |

*Immobilized anti-minor framework antibody, anti-major framework antibody detection.
+Normal subject.
++Actual cell numbers bearing the anti-minor framework antibody reactivity. It should be noted that the peripheral mononuclear cells contained about 2% cells which were reactive with the anti-minor framework antibody on the coated microtiter plate. Therefore it is necessary to normalize the actual positive cell count so as to compare it with the HPB-ALL T cell line. (See Table I).

TABLE VI

Detection of T Cell Antigen Receptor or Receptor Complex in the Cell Lysate of HPB-ALL T Cells*

| Coated Antibody | Detection Antibody | | |
|---|---|---|---|
| | Anti-Idiotype | Anti-Minor Framework | Anti-Major Framework |
| Anti-Idiotype | 0 | 0.456+ | >2 |
| Anti-Minor Framework | >2 | 0.190 | 1.526 |
| Anti-Major Framework | 1.543 | 0.969 | 0.55 |

+OD490 value.
*The cells were lysed witn NP40 as previously described herein; 2.5 million cells equivalent was used per assay well.

Detection of Released T Cell Antigen Receptor Complex in Sera

The presence of released T cell antigen receptor complex in culture supernates of T cell leukemic lines suggests that the released antigen receptor may be detected in the sera of patients with T cell leukemia and lymphoma. The following experiment was designed and performed to confirm this theory.

Microtiter wells from Immulon I plates were coated overnight at 4° C. with an anti-T3 monoclonal or control antibody at 2.5 μg/ml in PBS. The wells were then exhaustively washed, coated with 1% BSA in a buffer containing 0.025M Tris pH 7.4, 0.15M NaCl and 0.05% Tween 20 overnight at 4° C. and exhaustively washed again before the serum sample and T cell lysate were added. 50 μl of serum from leukemic patients and normal subjects were added to the coated wells, mixed with 10 μl of 2% digitonin and 40 μl of fetal calf serum, and incubated at room temperature for 15 minutes. The rest of the assay procedures were performed as described previously. As indicated in Table VII below, six serum samples from patients with T cell leukemia or T cell lymphoma had significantly elevated levels of released T cell antigen receptor complex over the normal subjects. It is contemplated that released T cell antigen receptors can be detected by using anti-receptor antibodies as the coated (immobilized) and the detection antibodies.

TABLE VII

Released T Cell Antigen Receptor Complex in Sera

| Serum Sample | OD490+ |
|---|---|
| *Patient A | 0.043 |
| B | 0.506 |
| C | 0.049 |
| D | 0.102 |
| E | 0.053 |
| F | 0.070 |
| **Normal Subject | 0.015 ± 0.0072 |

*Patients A and B were seropositive for human T cell leukemia virus I, and exhibited symptoms of T cell leukemia: Patient C was diagnosed as T cell leukemia; Patients D, E, and F were all diagnosed as T cell lymphoma.
**The average assay value of sera from 16 normal subjects (range of OD490 value: 0.01-0.031).
+Immobilized anti-T3 antibody with anti-major framework antibody detection Two hybridomas, each producing an anti-major framework T cell antigen receptor monoclonal antibody, have been deposited with the American Type Culture Collection, Rockville, Md., and have been assigned accession numbers HB 9282 and HB 9283, respectively.

References

1. J. Allison, B. McIntyre and D. Block, J. Immunol. 129, 2293-2300 (1982).

2. J. Kappler, R. Kubo, K. Haskins, C. Hannum, P. Marrack, M. Pigeon, B. McIntyre, J. Allison and I. Trowbridge, Cell 35, 295-302 (1983).

3. O. Acuto, S. Meuer, J. Hodgdon, S. Schlossman and E. Reinherz, J. Exp. Med 158, 1368-1373 (1983).

4. G. Siu, S.P.Clark, Y. Yoshikai, M. Malissen, Y. Yanagi, E. Strauss, T.W. Mak and L. Hood, Cell 37, 393 (1984).

5. Y. Yanagi, A. Chan, B. Chin, M. Minden and T.W. Mak, Proc. Natl. Acad. Sci. USA 82, 3430 (1985).

6. A. C. Hayday, H. Saito, S.D. Gillies, D.M. Kranz, G. Tanigawa, H.N. Eisen and S. Tonegawa, Cell 40 259-269 (1985).

7. S. Tonegawa, The Molecules of the Immune System, Scientific American, pps. 122-131, October 1985.

8. A. W. Boylston, R. D. Goldin, C.S. Moore, Eur. J. Immunol. 14, 273 (1984).

9. O. Acuto, T. J. Campen, H.D. Royer, R.E. Hussey, C.B. Poole and E.L. Reinherz, J. Exp. Med. 161, 1326 (1985).

10. R.D. Bigler, D.E. Fisher, C.Y. Wang, E.A. Rinnooykan and H. G. Kunkel, J. Exp. Med. 161, 1450 (1985).

11. M.B. Brenner, I.S. Trowbridge, J. McLean and J.L. Strominger, J. Exp. Med. 160, 541 (1984).

12. J. Ritz, T.J. Campen, R.E. Schmidt, H.D. Royer, T. Hercend, R.E. Hussey, E.L. Reniherz, Science 228, 1540 (1985).

13. M. Robertson, Nature 317, 768 (1985).

14. J. Borst, S. Alexander, J. Elder and C. Terhorst, J. Biol. Chem. 258, 5135 (1983).

15. P. Van den Elsen, G. Bruns, D.S. Gerhard, D. Pravtcheva, S. Jones, D. Housman, F.A. Ruddle, S. Orkin and C. Terhorst, Proc. Natl. Acad. Sci. USA 82, 2920 (1985).

16. P.S. Ohashi, T.W. Mak, P. Van den Elsen, Y. Yanagi, Y. Yoshikai, A.F. Calman, C. Terhorst, J.D. Stobo and A. Weiss, Nature 316, 606 (1985).

17. T. H. Watts, J. Gariepy, G.K. Schoolnik and H.M. McConnel, Proc. Natl. Acad. Sci. USA 82, 5480 (1985).

18. Bialy, Biotechnology 3, 858 (1985).

19. U. Krawinkel, M. Cramer, C. Berek, G. Hammerling, S.J. Black, K. Rajewski and K. Eichmann, Cold Spr. Harb. Symp. Quant. Biol. 4, 285 (1976).

20. H. Binz and H. Wigzell, Cold Spr. Harb. Symp. Quant. Biol. 4, 275 (1976).

21. H. Binz and H. Wigzell, J. Exp. Med. 154, 1261 (1981).

22. E. L. Reinherz, S. Meuer, K.A. Fitzgerald, R.E. Hussey, H. Levine and S.F. Schlossman, Cell 30, 735 (1982).

23. J. Fujimoto, S. Levy and R. Levy, J. Exp. Med. 159, 752 (1983).

24. L. A. Rubin, C.C. Kurman, M.E. Fritz, W.E. Biddison, B. Boutin, R. Yarchoan and David L. Nelson, J. Immunol. 135, 3172 (1985).

25. G.S. Bixler and M.Z. Atassi, Biotechnology 3, 47 (1985).

26. D.M. Kranz, H. Saito, C.M. Disteche, K. Swisshelm, D. Pravtcheva, F.H. Ruddle, H.N. Eisen and S. Tonegawa, Science 227, 941 (1985).

27. N. Caccia, M. Kronenberg, D. Saxe, R. Haars, G.A.P. Bruns, J. Goverman, M. Mallissen, H. Williard, Y. Yoshikai, M. Simon, L. Hood and T.W. Mak, Cell 37, 1091 (1984).

28. A. Rao, S.J. Faas and H. Cantor, Cell 36, 879 (1984).

29. Mayer, T.G., Fuller, T.C., Lazarovits, A.I., Boyle, L.A., Kurnick, J.T., J. Immunol. 134, 258 (1985).

30. Emmrich, F. and Meuer, S., Immunology Today 6, 197 (1985).

What is claimed is:

1. A method of monitoring in a subject a diseased condition caused by leukemia, lymphoma or viral infection characterized by the presence in a body fluid of the subject of an increase in quantity relative to healthy subjects of a molecule carrying an antigenic determinant of a T cell antigen receptor, which molecule is derived and spontaneously released from a T cell which comprises measuring the amount of the molecule in a series of body fluid samples taken over a period of time, identifying the presence or absence of an increase in quantity of the molecule in the body fluid samples over time and correlating the presence or absence of the increase with the diseased condition of the subject, in which the body fluid contains only such cell-free molecules carrying antigenic determinants of the T cell antigen receptor as are spontaneously released, and in which the T cell antigen receptor is a heterodimer consisting of monomers selected from the group consisting of the T cell antigen receptor alpha, beta, and gamma polypeptides.

2. A method for diagnosing in an animal a diseased state caused by leukemia, lymphoma or viral infection characterized by the presence in a body fluid of the animal of an increase in quantity relative to healthy animals of a molecule carrying an antigenic determinant of a T cell antigen receptor, which molecule is spontaneously released from a T cell which comprises detecting the increase in quantity of the molecule in the animal's body fluid and thereby diagnosing the diseased state, in which the body fluid contains only such cell-free molecules carrying antigenic determinants of the T cell antigen receptor as are spontaneously released, and in which the T cell antigen receptor is a heterodimer consisting of monomers selected from the group consisting of the T cell antigen receptor alpha, beta, and gamma polypeptides.

3. The method of claim 2 in which the increase in quantity of the molecule is detected by contacting a sample of the animal's body fluid with a known amount of a reagent which specifically binds to the antigenic determinant so as to form a reaction complex between the reagent and the molecule, determining the amount of reaction complex so formed, determining therefrom the amount of the molecule in the sample, and comparing the amount of the molecule so determined with the amount present in a sample from a healthy animal.

4. A method for diagnosing in a human subject a diseased state caused by leukemia, lymphoma or viral infection characterized by the presence in a body fluid of the subject of an increase in quantity relative to healthy humans of a molecule carrying an antigenic determinant of a T cell antigen receptor, which molecule is spontaneously released from a T cell which comprises detecting the increase in quantity of the molecule in the subject's body fluid and thereby diagnosing the diseased state, in which the body fluid contains only such cell-free molecules carrying antigenic determinants of the T cell antigen receptor as are spontaneously released, and in which the T cell antigen receptor is a heterodimer consisting of monomers selected from the group consisting of the T cell antigen receptor alpha, beta, and gamma polypeptides.

5. The method of claim 4 in which the increase in quantity of the molecule is detected by contacting a sample of the subject's body fluid with a known amount of a reagent which specifically binds to the antigenic determinant so as to form a reaction complex between the reagent and the molecule, determining the amount of reaction complex so formed, determining therefrom the amount of the molecule in the sample, and comparing the amount of the molecule so determined with the amount present in a sample from a healthy subject.

6. A method of claim 5, wherein the body fluid is blood, plasma, serum, urine, spinal fluid, synovial fluid, amnionic fluid or cranial fluid.

7. method of claim 5, wherein the molecule is a fragment of the T cell antigen receptor.

8. A method of claim 5, wherein the reagent is labelled with a marker.

9. A method of claim 8, wherein the marker is a fluorescent dye.

10. A method of claim 8, wherein the marker is a radioactive isotope.

11. A method of claim 8, wherein the marker is an enzyme which catalyses a reaction producing a detectable product.

12. A method of claim 5, wherein the reagent is an antibody.

13. A method of claim 12, wherein the antibody is a monoclonal antibody.

14. A method of claim 8, wherein the reagent is a lectin.

15. A method of claim 5, wherein the antigenic determinant is on the antigen receptor of more than 20% of all T cells.

16. A method of claim 15, wherein the reagent is an anti-major framework antibody.

17. A method of claim 5, wherein the antigenic determinant is on the antigen receptor of less than 20% of T cells.

18. A method of claim 17, wherein the reagent is an anti-minor framework antibody.

19. A method of claim 5, wherein the antigen determinant is on the antigen receptor of one T cell clone.

20. A method of claim 19, wherein the reagent is an anti-idiotypic antibody.

21. A method of claim 5, wherein the molecule is complexed to a T3 protein.

22. A method of claim 5, wherein the method for determining the amount of the molecule further comprises contacting the sample with a second reagent labelled with a marker so as to form a second reaction complex among the reagent which specifically binds to the antigenic determinant, the second reagent and the molecule, determining the amount of second reaction complex so formed, and determining therefrom the amount of the molecule in the sample.

23. A method of claim 22, wherein the first reagent is an anti-major framework antibody and the second reagent is an anti-receptor antibody or a lectin.

24. A method of claim 22, wherein the first reagent is an anti-minor framework antibody and the second reagent is an anti-receptor antibody or a lectin.

25. A method of claim 22, wherein the first reagent is an anti-idiotypic antibody and the second reagent is an anti-receptor antibody or a lectin.

26. A method for diagnosing in a subject a diseased state caused by leukemia, lymphoma or viral infection characterized by the presence in a body fluid of the subject of an increase in quantity relative to healthy subjects of a molecule carrying an antigenic determinant of a T cell antigen receptor, which molecule (i) is derived and spontaneously released from a T cell, and (ii) is complexed to a T3 protein, which method comprises contacting a sample of the subject's body fluid with a known amount of a reagent which specifically binds to the antigenic determinant so as to form a reaction complex between the reagent and the molecule, determining the amount of reaction complex so formed, determining therefrom the amount of the molecule in the sample, comparing the amount of the molecule so determined with the amount present in a sample from a healthy subject, and thereby detecting the increase in quantity, in which the sample contains only such cell-free molecules carrying antigenic determinants of the T cell antigen receptor as are spontaneously released, and in which the T cell antigen receptor is a heterodimer consisting of monomers selected from the group consisting of the T cell antigen receptor alpha, beta, and gamma polypeptides.

27. A method of claim 26, wherein the method for determining the amount of the molecule further comprises contacting the sample with a second reagent which specifically binds to the T3 protein so as to form a reaction complex between the second reagent and the T3 protein, determining the amount of any reaction complexes formed which comprise the second reagent and the reagent which specifically binds to the antigenic determinant, and the molecule, and determining therefrom the amount of the molecule in the sample.

28. A method of claim 27, wherein the second reagent is an anti-T3 antibody and the first reagent is an anti-receptor antibody or a lectin.

29. A method for dianosing in a subject a diseased state caused by leukemia, lymphoma or viral infection characterized by the presence in a body fluid sample of the subject of an increase in quantity relative to healthy subjects of a molecule carrying an antigenic determinant of a T cell antigen receptor, which molecule (i) is spontaneously released from a T cell and (ii) is complexed to a T3 protein, which comprises detecting the increase in quantity of said molecule in a body fluid sample and thereby diagnosing the diseased state, which method comprises:
 (a) contacting the sample with a first reagent which specifically binds to the antigenic determinant so as to form a reaction complex between the reagent and the molecule;
 (b) contacting the sample with a second reagent which specifically binds to the T3 protein so as to form a reaction complex between the second reagent and the T3 protein; and
 (c) detecting the presence of any reaction complexes comprising the first and second reagents and thereby detecting the molecule, in which the sample contains only such cell-free molecules carrying antigenic determinants of the T cell antigen receptor as are spontaneously released, and in which the T cell antigen receptor is a heterodimer consisting of monomers selected from the group consisting of the T cell antigen receptor alpha, beta, and gamma polypeptides.

* * * * *